US009123155B2

(12) United States Patent
Cunningham et al.

(10) Patent No.: US 9,123,155 B2
(45) Date of Patent: Sep. 1, 2015

(54) APPARATUS AND METHOD FOR USING AUGMENTED REALITY VISION SYSTEM IN SURGICAL PROCEDURES

(75) Inventors: James S. Cunningham, Boulder, CO (US); Peter M. Mueller, Frederick, CO (US); James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 522 days.

(21) Appl. No.: 13/206,040

(22) Filed: Aug. 9, 2011

(65) Prior Publication Data

US 2013/0038707 A1 Feb. 14, 2013

(51) Int. Cl.
*A62B 1/04* (2006.01)
*G06T 19/00* (2011.01)
*H04N 7/18* (2006.01)
*A61B 1/00* (2006.01)
*G06K 9/00* (2006.01)

(52) U.S. Cl.
CPC ............. *G06T 19/006* (2013.01); *A61B 1/0005* (2013.01); *A61B 1/00009* (2013.01); *G06K 9/00671* (2013.01); *H04N 7/183* (2013.01); *G06T 2210/41* (2013.01); *G09G 2340/125* (2013.01); *G09G 2380/08* (2013.01)

(58) Field of Classification Search
CPC . G06T 2210/41; H04N 7/183; G09G 2380/08
USPC ............. 606/130; 715/771; 348/65; 434/267; 600/407–480; 382/128–132; 726/19
See application file for complete search history.

(56) References Cited

U.S. PATENT DOCUMENTS

| 6,223,100 | B1 | 4/2001 | Green |
| 2006/0174133 | A1* | 8/2006 | Obata .......................... 713/182 |
| 2008/0243142 | A1* | 10/2008 | Gildenberg ................... 606/130 |
| 2009/0036902 | A1* | 2/2009 | DiMaio et al. ................ 606/130 |
| 2009/0257635 | A1* | 10/2009 | Harvey et al. ................. 382/131 |
| 2010/0167250 | A1* | 7/2010 | Ryan et al. ..................... 434/267 |
| 2010/0228249 | A1 | 9/2010 | Mohr et al. |
| 2011/0060214 | A1* | 3/2011 | Makower ....................... 600/424 |
| 2011/0225530 | A1* | 9/2011 | Osmundson et al. .......... 715/771 |
| 2012/0100517 | A1* | 4/2012 | Bowditch et al. ............. 434/267 |

FOREIGN PATENT DOCUMENTS

WO WO 01/01847 1/2001

* cited by examiner

*Primary Examiner* — Tung Vo
*Assistant Examiner* — Rowina Cattungal

(57) ABSTRACT

A system and method for improving a surgeon's vision by overlaying augmented reality information onto a video image of the surgical site. A high definition video camera sends a video image in real time. Prior to the surgery, a pre-operative image is created from MRI, x-ray, ultrasound, or other method of diagnosis using imaging technology. The pre-operative image is stored within the computer. The computer processes the pre-operative image to decipher organs, anatomical geometries, vessels, tissue planes, orientation, and other structures. As the surgeon performs the surgery, the AR controller augments the real time video image with the processed pre-operative image and displays the augmented image on an interface to provide further guidance to the surgeon during the surgical procedure.

32 Claims, 9 Drawing Sheets

APPARATUS AND METHOD FOR USING AUGMENTED REALITY VISION SYSTEM IN SURGICAL PROCEDURES

BACKGROUND

1. Technical Field

The present disclosure relates to a display system and method for assisting a surgeon during surgery and, more particularly, to an augmented reality display system that incorporates pre-operative images into a real time video signal to assist a surgeon during surgery.

2. Background of Related Art

Minimally invasive surgical procedures typically employ small incisions in body cavities for access of various surgical instruments, including forceps, laparoscopes, scalpels, scissors, and the like. It is often the case that several surgical hands, such as several laparoscopic instrument and camera holders, are necessary to hold these instruments for the operating surgeon during the particular surgical procedure. With the introduction of robotic-assisted minimally invasive surgery (MIS) in recent years, hospitals worldwide have made significant investments in acquiring this latest technology for their respective facilities.

Thus, it is known to use robotic-assisted MIS when carrying out surgical operations. When surgery of this kind is performed, access to a subcutaneous surgical site is provided via a number (typically 3 to 5) of small (typically 5-12 mm) incisions, through which a surgical arm is manually passed. The surgical arms are then coupled to the surgical robotic instrument, which is capable of manipulating the surgical arms for performing the surgical operations, such as suturing or thermally cutting through tissue and cauterizing blood vessels. The surgical arms thus extend through the incisions during the surgery, one of which incisions is used for supplying a gas, in particular carbon dioxide, for inflating the subcutaneous area and thus create free space at that location for manipulating the surgical instruments.

Therefore, open surgeries often require a surgeon to make sizable incisions to a patient's body in order to have adequate visual and physical access to the site requiring treatment. The application of laparoscopy for performing procedures is commonplace. Laparoscopic surgeries are performed using small incisions in the abdominal wall and inserting a small endoscope into the abdominal cavity and transmitting the images captured by the endoscope onto a visual display. The surgeon may thus see the abdominal cavity without making a sizable incision in the patient's body, reducing invasiveness and providing patients with the benefits of reduced trauma, shortened recovery times, and improved cosmetic results. In addition to the endoscope, laparoscopic surgeries are performed using long, rigid tools inserted through incisions in the abdominal wall.

However, conventional techniques and tools for performing laparoscopic procedures may limit the dexterity and vision of the surgeon. Given the size of the incisions, the maneuverability of the tools is limited and additional incisions may be required if an auxiliary view of the surgical site is needed. Thus, robotic instruments may be used to perform laparoscopic procedures.

One example of a robotic assisted MIS system is the da Vinci® System that includes an ergonomically designed surgeon's console, a patient cart with four interactive robotic arms, a high performance vision system, and instruments. The da Vinci® console allows the surgeon to sit while viewing a highly magnified 3D image of the patient's interior sent from the high performance vision system. The surgeon uses master controls on the console that work like forceps to perform the surgery. The da Vinci® system responds to the surgeon's hand, wrist, and finger movements into precise movements of the instruments within the patient's interior.

However, conventional techniques and tools for performing laparoscopic procedures may limit the vision of the surgeon.

SUMMARY

In accordance with the present disclosure, a system and method for improving a surgeon's vision by overlaying augmented reality information onto a real time video image of the surgical site and adjusting the augmented reality information as the video image changes. A high definition video camera sends a video image in real time to a computer. Prior to the surgery, a pre-operative image is created from an MRI, x-ray, ultrasound, or other method of diagnosis using imaging technology. The pre-operative image is stored within the computer. The computer processes the pre-operative image to decipher organs, anatomical geometries, vessels, tissue planes, orientation, and other structures. As the surgeon performs the surgery, the computer augments the real time video image with the processed pre-operative image and displays the augmented image on an interface to provide further guidance to the surgeon during the surgical procedure.

In another embodiment of the present disclosure, the computer deciphers the preoperative image to create boundaries around organs, tissue, or other delicate structures of the patient. The boundaries can create a safety zone for example around an organ to prevent the surgeon from inadvertently contacting the organ while performing the surgery. The safety boundaries can prevent an instrument from entering the zone by providing haptic feedback to the surgeon that the instrument is near a delicate structure. In an alternative embodiment, if the instrument is a robotic tool, the robotic tool can be prevented from entering the safety zone by stopping a drive assembly of the instrument.

According to an embodiment of the present disclosure, a method for augmenting a video signal with data includes the steps of generating a pre-operative image of an anatomical section of a patient and generating a video image of a surgical site within the patient. The method also includes the steps of processing the pre-operative image to generate data about the anatomical section of the patient and embedding the data within the video image to supply an augmented reality display to a user about the anatomical section of the patient.

According to another embodiment of the present disclosure, a method for augmenting a safety zone onto a video signal comprises storing a pre-operative image of an anatomical section of a patient and analyzing the pre-operative image to determine a safety zone around an anatomical body within the patient, wherein the anatomical body is located within the anatomical section. The method further includes the steps of receiving a video signal from a camera located within the patient during a surgical procedure, augmenting the safety zone onto the video signal, and displaying the video signal with the safety zone.

According to another embodiment of the present disclosure, a system for augmenting a video signal with data comprises a pre-operative image, a camera, and a controller. The pre-operative image is generated of an anatomical section of a patient. The camera is configured to send real time video signal from the patient to a controller. The controller is configured to analyze the pre-operative image to gather data about the anatomical section, and to augment the data about the anatomical section onto the video signal and a user interface configured to display the video signal and the augmented data.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1A:
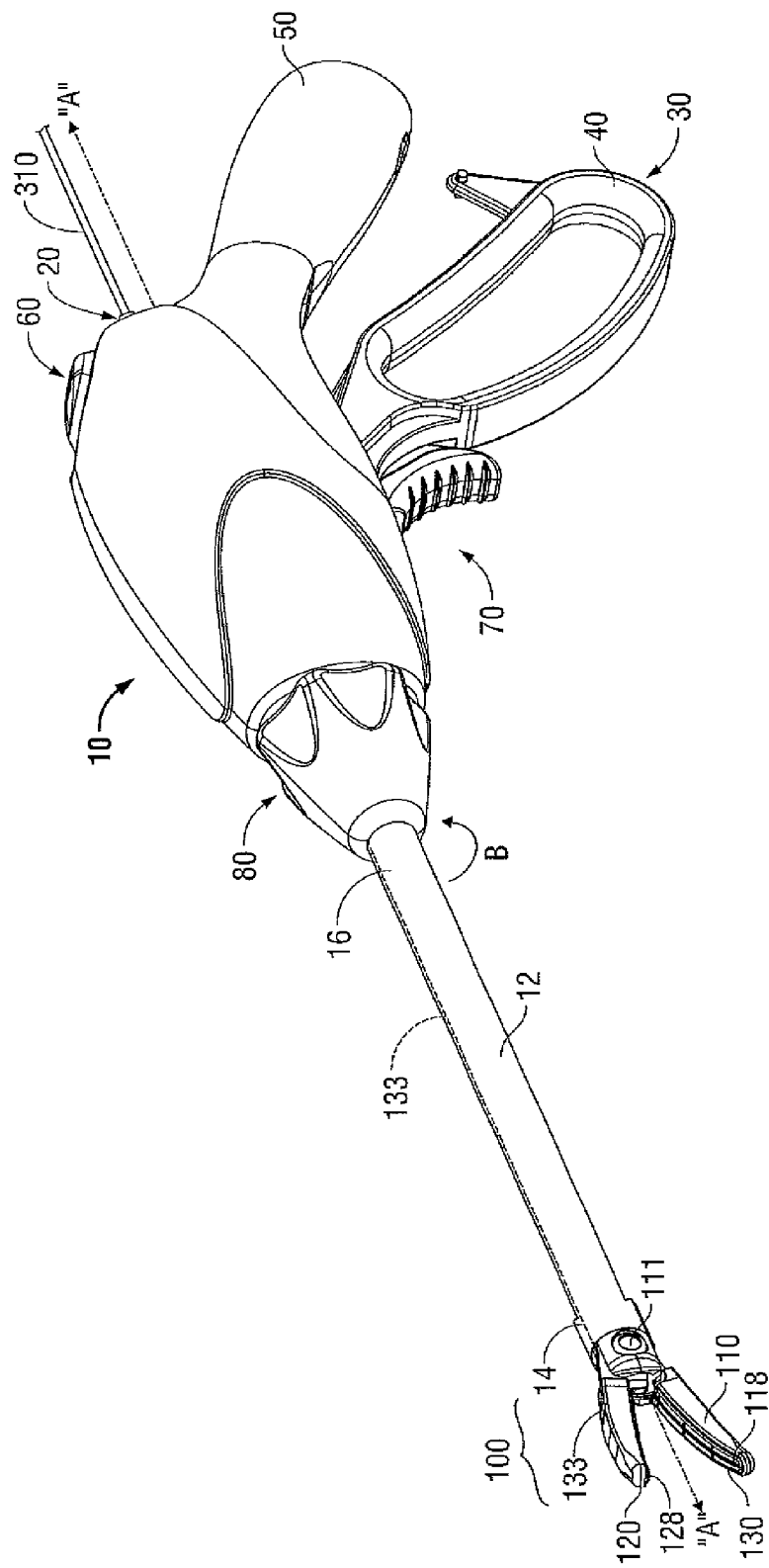
FIG. 1A is a side, perspective view of an endoscopic bipolar forceps showing an end effector assembly including jaw members according to an embodiment of the present disclosure.
Figure 1B:
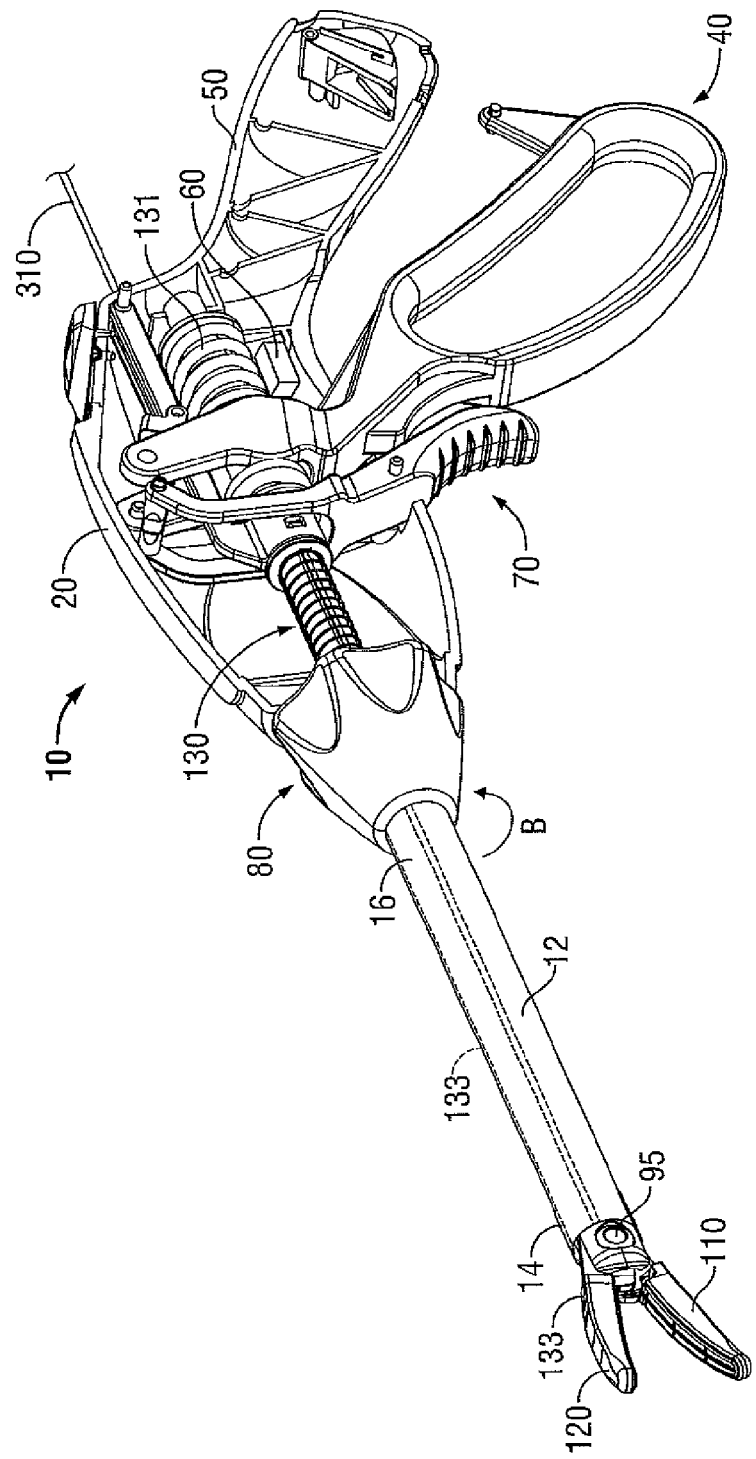
FIG. 1B is a side, perspective view of the endoscopic bipolar forceps depicted in FIG. 1A illustrating internal components associated with a handle assembly of the endoscopic bipolar forceps.

With reference to FIGS. 1A and 1B, an illustrative embodiment of an electrosurgical surgical tool, e.g., a bipolar forceps 10 (forceps 10) is shown. Forceps 10 is operatively and selectively coupled to an electrosurgical generator (not shown) for performing an electrosurgical procedure. As noted above, an electrosurgical procedure may include sealing, cutting, cauterizing coagulating, desiccating, and fulgurating tissue all of which may employ RF energy. The electrosurgical generator may be configured for monopolar and/or bipolar modes of operation and may include or be in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., an electrosurgical cable 310) to the forceps 10.

Forceps 10 is shown configured for use with various electrosurgical procedures and generally includes a housing 20, electrosurgical cable 310 that connects the forceps 10 to the electrosurgical generator, a rotating assembly 80 and a trigger assembly 70. For a more detailed description of the rotating assembly 80, trigger assembly 70, and electrosurgical cable 310 (including line-feed configurations and/or connections), reference is made to commonly-owned U.S. patent application Ser. No. 11/595,194 filed on Nov. 9, 2006, now U.S. Patent Publication No. 2007/0173814.

With continued reference to FIGS. 1A and 1B, forceps 10 includes a shaft 12 that has a distal end 14 configured to mechanically engage an end effector assembly 100 operably associated with the forceps 10 and a proximal end 16 that mechanically engages the housing 20. In the drawings and in the descriptions that follow, the term "proximal," as is traditional, will refer to the end of the forceps 10 which is closer to the user, while the term "distal" will refer to the end that is farther from the user.

Handle assembly 30 includes a fixed handle 50 and movable handle 40. In one particular embodiment, fixed handle 50 is integrally associated with housing 20 and handle 40 is movable relative to fixed handle 50 for effecting movement of one or more components, e.g., a drive wire 133, operably associated with a drive assembly 130 (FIG. 1B) via one or more suitable mechanical interfaces, e.g., a linkage interface, gear interface, or combination thereof.

Drive assembly 130 is in operative communication with handle assembly 30 (see FIGS. 1A and 1B) for imparting movement of one or both of a pair of jaw members 110, 120 of end effector assembly 100, described in greater detail below. The drive assembly 130 may include a compression spring 131 (shown separated from housing 20) or a drive wire 133 to facilitate closing the jaw members 110 and 120 around pivot pin 111. Drive wire 133 is configured such that proximal movement thereof causes one movable jaw member, e.g., jaw member 120, and operative components associated therewith, e.g., a seal plate 128, to "flex" or "bend" inwardly substantially across a length thereof toward the other jaw member, e.g., jaw member 110. With this purpose in mind, drive rod or wire 133 may be made from any suitable material and is proportioned to translate within the shaft 12. In the illustrated embodiments, drive wire 133 extends through the shaft 12 past the distal end 14, see FIG. 1A for example.

In an alternative embodiment, the electrosurgical tool may be a pencil, ultrasonic instrument, or other handheld surgical instrument.

Figure 2:
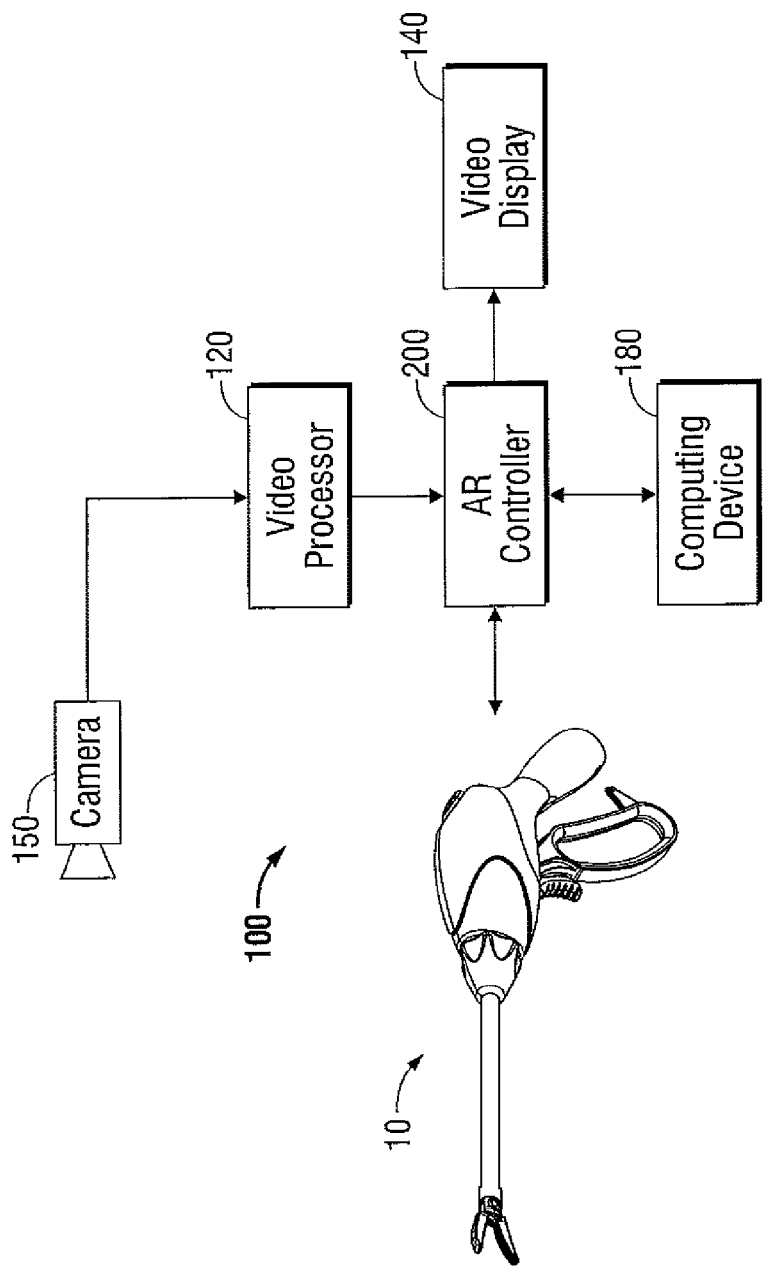
FIG. 2 is a schematic diagram of an augmented reality controller system in accordance with an embodiment of the present disclosure.

FIG. 2 illustrates a schematic diagram of an augmented reality controller system 100 in accordance with an embodiment of the present disclosure. With reference to FIG. 2, the augmented reality (AR) controller 200 is configured to store data transmitted to AR controller 200 by a surgical tool 10 as well as process and analyze the data. The surgical tool 10 can be a handheld activated laparoscopic tool or a robotic tool. The AR controller 200 is also connected to other devices, such as a video display 140, a video processor 120 and a computing device 180 (e.g., a personal computer, a PDA, a smartphone, a storage device, etc.). The video processor 120 may be used for processing output data generated by the AR controller 200 for output on the video display 140. Additionally, the video processor 120 receives a real time video signal from a camera 150 inserted into the patient during the surgical procedure. The computing device 180 is used for additional processing of the pre-operative imaged data. In one embodiment, the results of pre-operative imaging such as an ultrasound, MRI, x-ray, or other diagnosing image may be stored internally for later retrieval by the computing device 180.

The AR controller 200 includes a data port 260 (FIG. 3) coupled to the microcontroller 250 which allows the AR controller 200 to be connected to the computing device 180. The data port 130 may provide for wired and/or wireless communication with the computing device 180 providing for an interface between the computing device 180 and the AR controller 200 for retrieval of stored pre-operative imaging data, configuration of operating parameters of the AR controller 200 and upgrade of firmware and/or other software of the AR controller 200.

Figure 3:
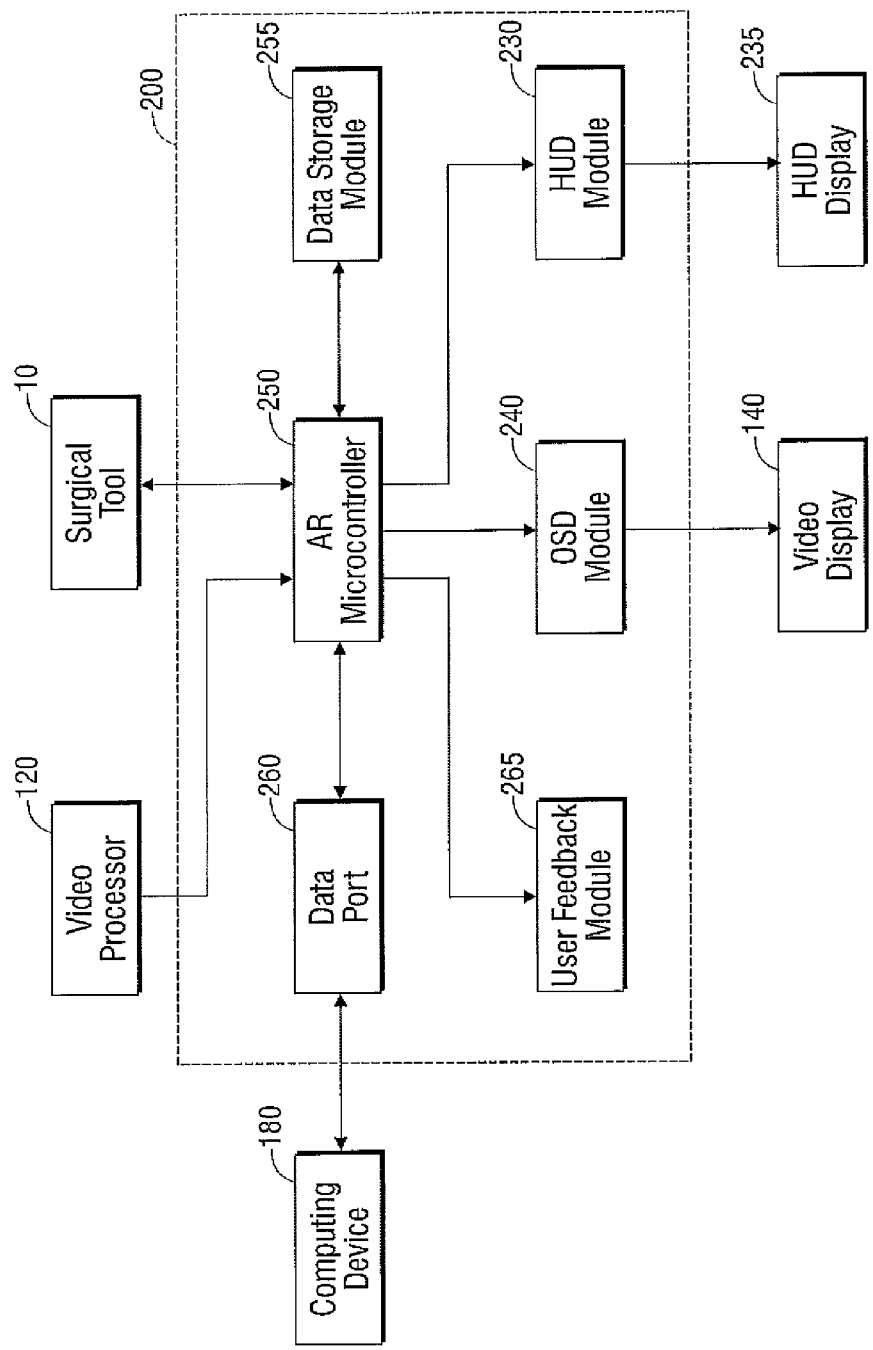
FIG. 3 is a schematic diagram of an augmented reality controller system in accordance with an embodiment of the present disclosure.

Components of the AR controller 200 are shown in FIG. 3. The AR controller 200 may include a microcontroller 250, a data storage module 255 a user feedback module 265, an OSD module 240, a HUD module 230, and a data port 260.

The data storage module 255 may include one or more internal and/or external storage devices, such as magnetic hard drives, flash memory (e.g., Secure Digital® card, Compact Flash® card, or MemoryStick®). The data storage module 255 is used by the AR controller 200 to store data from the surgical tool 10 for later analysis of the data by the computing device 180. The data may include information supplied by a sensor 315 (FIG. 4), such as a motion sensor or other sensors disposed within the surgical tool 10.

Figure 4:
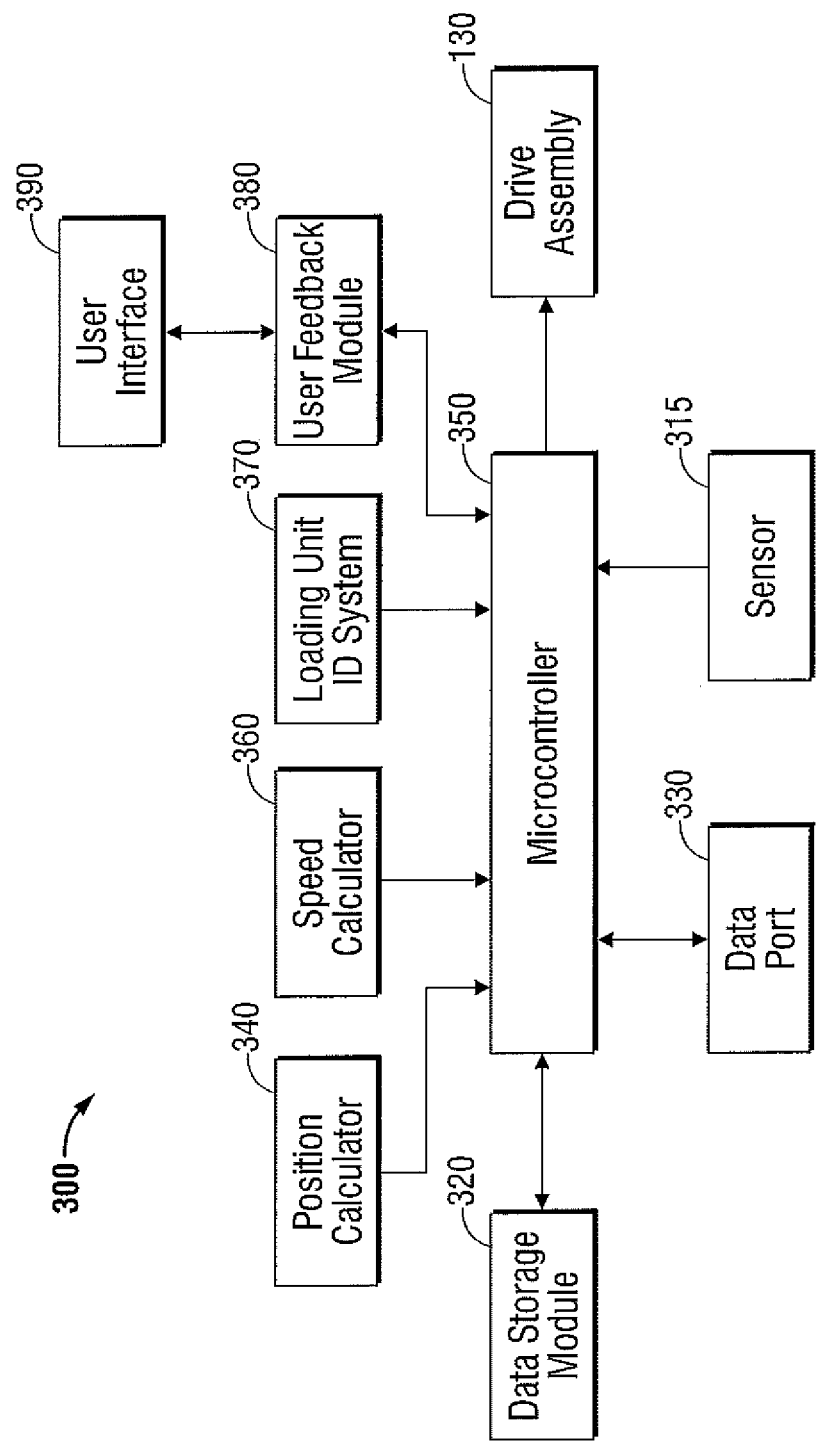
FIG. 4 is a schematic diagram of a tool control system in accordance with an embodiment of the present disclosure.

The microcontroller 250 may supplant, complement, or supplement the control circuitry 300 of the surgical tool 10 shown in FIG. 4. The microcontroller 250 includes internal memory which stores one or more software applications (e.g., firmware) for controlling the operation and functionality of the surgical tool 10. The microcontroller 250 processes input data from the computing device 130 and adjusts the operation of the surgical tool 10 in response to the inputs. The surgical tool 10 is configured to connect to the AR controller 200 wirelessly or through a wired connection via a data port 330. The microcontroller 250 is coupled to the user feedback module 265 which is configured to inform the user of operational parameters of the surgical tool 10. The user feedback module 265 may be coupled to a haptic mechanism 60 within the surgical tool 10 or a remote (not shown) to provide haptic or vibratory. The haptic mechanism 60 may be an asynchronous motor that vibrates in a pulsating manner. In one embodiment, the vibrations are at a frequency of about 30 Hz or above, providing a displacement having an amplitude of 1.5 mm or lower to limit the vibratory effects from reaching the end effector assembly 100. The haptic feedback can be increased or decreased in intensity. For example, the intensity of the feedback may be used to indicate that the forces on the instrument are becoming excessive. In alternative embodiments, the user feedback module 265 may also include visual and/or audible outputs.

The microcontroller 250 outputs data on video display 140 and/or the heads-up display (HUD) 235. The video display 140 may be any type of display such as an LCD screen, a plasma screen, electroluminescent screen and the like. In one embodiment, the video display 140 may include a touch screen and may incorporate resistive, surface wave, capacitive, infrared, strain gauge, optical, dispersive signal or acoustic pulse recognition touch screen technologies. The touch screen may be used to allow the user to provide input data while viewing AR video. For example, a user may add a label identifying the surgeon for each tool on the screen. The HUD display 235 may be projected onto any surface visible to the user during surgical procedures, such as lenses of a pair of glasses and/or goggles, a face shield, and the like. This allows the user to visualize vital AR information from the AR controller 200 without losing focus on the procedure.

The AR controller 200 includes an on-screen display (OSD) module 240 and a HUD module 230. The modules 240, 230 process the output of the microcontroller 250 for display on the respective displays 140 and 235. More specifically, the OSD module 240 overlays text and/or graphical information from the AR controller 250 over video images received from the surgical site via camera 150 (FIG. 2) disposed therein. Specifically, the overlaid text and/or graphical information from the AR controller 250 includes computed data from pre-operative images, such as x-rays, ultrasounds, MRIs, and/or other diagnosing images. The computing devices 180 stores the one or more pre-operative images. In an alternative embodiment, the data storage module 255 can store the pre-operative image. The AR controller 200 processes the one or more pre-operative images to determine margins and location of an anatomical body in a patient, such as an organ or a tumor. Alternatively, the computing device 180 can process and analyze the pre-operative image. Additionally, the AR controller 200 can create safety boundaries around delicate structures, such as an artery or organ. Further, the AR controller 200 can decipher the one or more pre-operative images to define and label structures, organs, anatomical geometries, vessels, tissue planes, orientation, and other similar information. Additionally, information about which surgeon is holding each tool can be determined by the AR controller either through user input or a sensor on the tool and the surgeon. The AR controller overlays the information processed from the one or more pre-operative images onto a real time video signal from the camera 150 within the patient. The augmented video signal including the overlaid information is transmitted to the video display 140 allowing the user to visualize more information about the surgical site. Additionally, as the camera is moved around the surgical site, the augmented information moves to overlay on the appropriate structures. For example, if a liver is located on the right hand side of the video image, the liver is shown with the augmented information. The augmented information includes an outline of the liver and a label for the liver. If the camera is moved and the liver is now on the left hand side of the video image, then the label and outline are moved to the left side of the display and overlaid on the liver.

FIG. 4 illustrates a control system 300 including the microcontroller 350 which is coupled to the position and speed calculators 340 and 360, the loading unit identification system 370, the user interface 390, the drive assembly 130, and a data storage module 320. In addition the microcontroller 350 may be directly coupled to a sensor 315, such as a motion sensor, torque meter, ohm meter, load cell, current sensor, etc.

The microcontroller 350 includes internal memory which stores one or more software applications (e.g., firmware) for controlling the operation and functionality of the surgical tool 10. The microcontroller 350 processes input data from the user interface 390 and adjusts the operation of the surgical tool 10 in response to the inputs.

The microcontroller 350 is coupled to the user interface 390 via a user feedback module 380 which is configured to inform the user of operational parameters of the surgical tool 10. The user feedback module 380 instructs the user interface 390 to output operational data on an optional video display. In particular, the outputs from the sensors are transmitted to the microcontroller 350 which then sends feedback to the user instructing the user to select a specific mode or speed for the surgical tool 10 in response thereto.

The loading unit identification system 370 instructs the microcontroller 350 which end effector assembly 100 is attached to the surgical tool 10. In an embodiment, the control system 300 is capable of storing information relating to the force applied the end effector assembly 100, such that when a specific end effector assembly 100 is identified the microcontroller 350 automatically selects the operating parameters for the surgical tool 10. For example, torque parameters could be stored in data storage module 320 for a laparoscopic grasper.

The microcontroller 350 also analyzes the calculations from the position and speed calculators 340 and 360 and other sensors to determine the actual position, direction of motion, and/or operating status of components of the surgical tool 10.

The analysis may include interpretation of the sensed feedback signal from the calculators 340 and 360 to control the movement of the drive assembly 130 and other components of the surgical instrument 10 in response to the sensed signal. The microcontroller 350 may be configured to limit the travel of the end effector assembly 100 once the end effector assembly 100 has moved beyond a predetermined point as reported by the position calculator 340. Specifically, if the microcontroller determines that the position of the end effector assembly 100 is within a safety zone determined by the AR controller 200, the microcontroller is configured to stop the drive assembly 130. Alternatively, the position of the surgical tool 10 may be calculated using the method disclosed in U.S. Ser. No. 12/720,881, entitled "System and Method for Determining Proximity Relative to a Critical Structure" filed on Mar. 10, 2010, which is hereby incorporated by reference.

In one embodiment, the surgical tool 10 includes various sensors 315 configured to measure current (e.g., an ammeter), resistance (e.g., an ohm meter), and force (e.g., torque meters and load cells) to determine loading conditions on the end effector assembly 100. During operation of the surgical tool 10 it is desirable to know the amount of force exerted on the tissue for a given end effector assembly 100. For "softer" tissue the haptic mechanism 60 could vibrate the handle assembly 30 at a low frequency. As the tissue changes, an increased load may need to be applied for the same end effector assembly 100, the haptic mechanism 60 may vibrate at the handle assembly 30 at a higher frequency to inform the surgeon to apply more pressure on the tissue. Detection of abnormal loads (e.g., outside a predetermined load range) indicates a problem with the surgical tool 10 and/or clamped tissue which is communicated to the user through haptic feedback. Additionally, impedance sensors or other sensors can be used to distinguish between a target tissue and a different kind of tissue. Different tactile feedback can then be sent to the surgeon through the haptic mechanism 60 for the target tissue and the different kind of tissue to allow the surgeon to "feel" tissue with the tool 10. For example, the haptic mechanism may send long slow pulses for the target tissue and short quick pulses for the different kind of tissue.

The data storage module 320 records the data from the sensors coupled to the microcontroller 350. In addition, the data storage module 320 may record the identifying code of the end effector assembly 100, user of surgical tool, and other information relating to the status of components of the surgical tool 10. The data storage module 320 is also configured to connect to an external device such as a personal computer, a PDA, a smartphone, or a storage device (e.g., a Secure Digital™ card, a CompactFlash card, or a Memory Stick™) through a wireless or wired data port 330. This allows the data storage module 320 to transmit performance data to the external device for subsequent analysis and/or storage. The data port 330 also allows for "in the field" upgrades of the firmware of the microcontroller 350.

Embodiments of the present disclosure may include an augmented reality (AR) control system as shown in FIGS. 2-3. The system includes the AR controller 200. The surgical tool 10 is connected to the AR controller 200 via the data port 330 which may be either wired (e.g., FireWire®, USB, Serial RS232, Serial RS485, USART, Ethernet, etc.) or wireless (e.g., Bluetooth®, ANT3®, KNX®, Z-Wave®, X10®, Wireless USB®, Wi-Fi IrDA®, nanoNET®, TinyOS®, ZigBee®, 802.11 IEEE, and other radio, infrared, UHF, VHF communications and the like).

Figure 5:
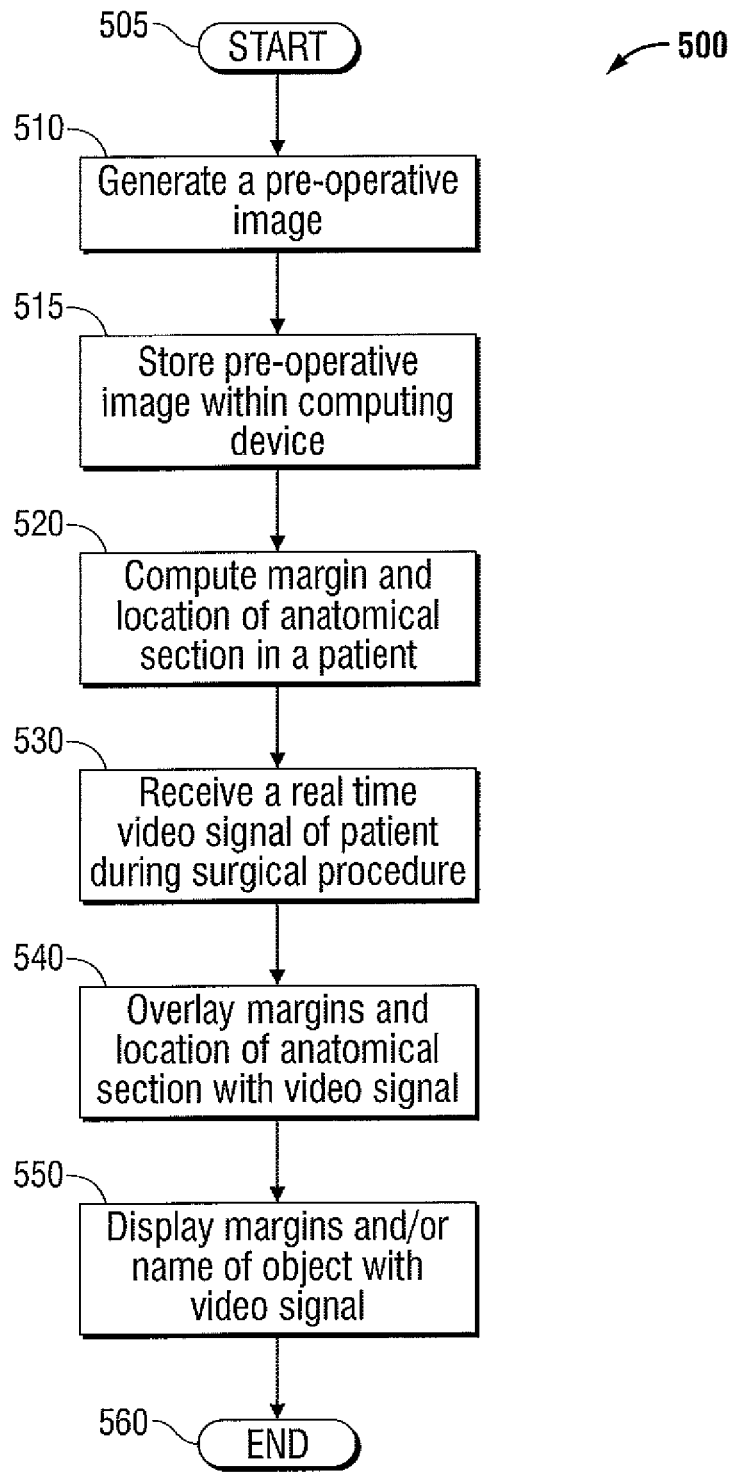
FIG. 5 is a flow diagram of a process for augmenting information onto a video signal in accordance with an embodiment of the present disclosure.

FIG. 5 is a flow diagram of a process 500 for augmenting information onto a video signal according to an embodiment of the invention. After the process 500 starts at step 505, a pre-operative image is generated from a diagnosing imaging source, such as from an MRI, ultrasound, x-ray, CAT scan, etc. at step 510. The pre-operative image is taken of an anatomical section of the patient, which may include organs, tissue, vessels, bones, tumors, muscles, etc. Multiple images can be generated from one or more sources based on the information required by the surgeon. Next, the pre-operative image is stored within a computing device 180 at step 515. The computing device analyzes the pre-operative image and computes margins and location of the anatomical section at step 520. Prior to starting the surgery, a camera 150 is inserted within the patient. A real time video signal of the patient during the surgical procedure is received at AR controller 200 during the surgical procedure at step 530. The margins and location the anatomical section are overlaid onto the video signal at step 540. Before the process 500 ends at step 560, the margins and location the anatomical section are displayed with the video signal. For example, if the anatomical section is a tumor then the location and margins of the tumor are calculated and then tumor is outlined and labeled on the real time video signal to displayed to the surgeon.

Figure 6:
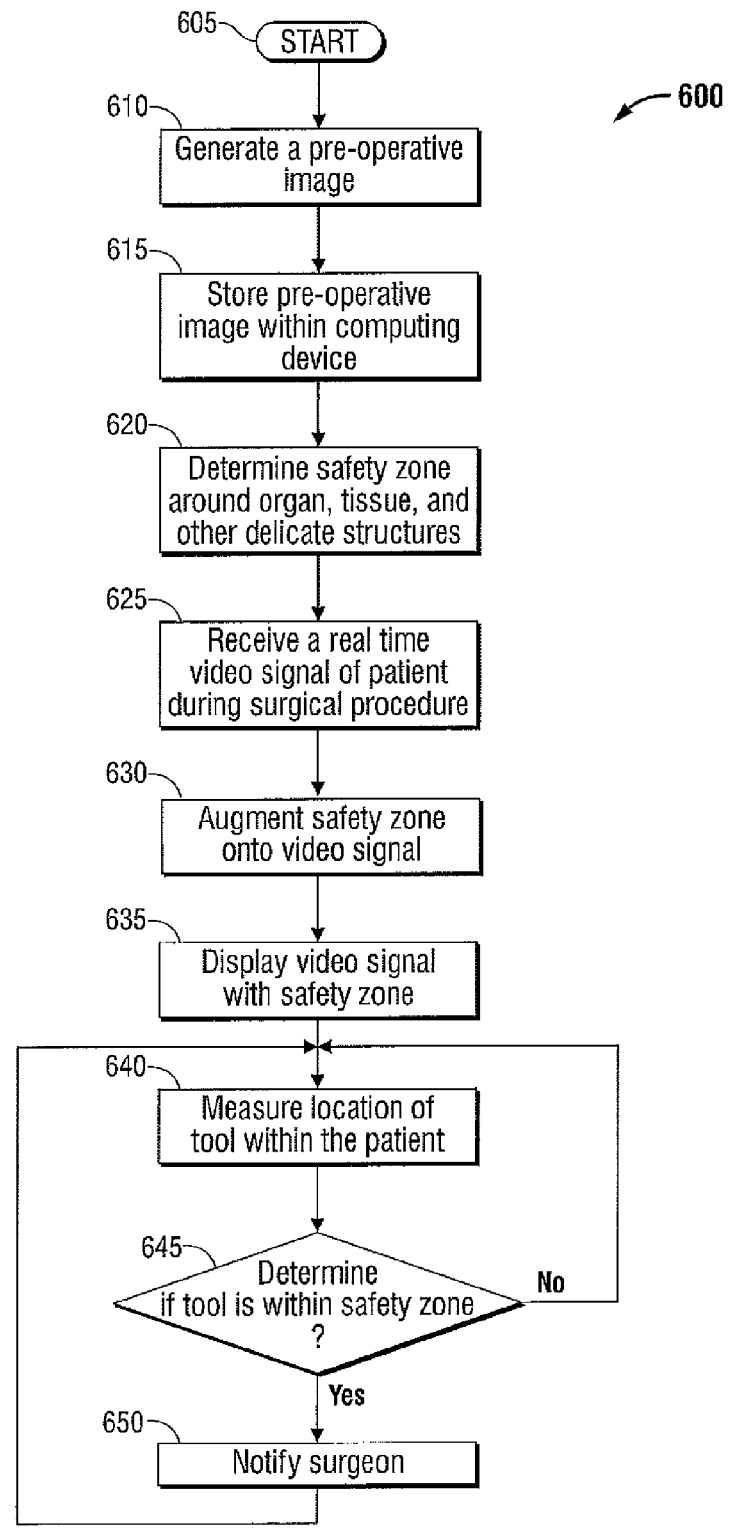
FIG. 6 is a flow diagram of a process for augmenting a safety zone onto a video signal in accordance with an embodiment of the present disclosure.

FIG. 6 is a flow diagram of process 600 for augmenting a safety zone onto a video signal according to an embodiment of the invention. After the process 600 starts at step 605, a pre-operative image of an anatomical section of a patient is generated at step 610. The pre-operative image can be generated from any type of diagnosing image, such as an x-ray, MRI, CAT scan, ultrasound, etc. The pre-operative image is then stored within a computing device 180 at step 615. Next, the computing device analyzes the pre-operative image determines a safety zone around organs, tissue, and/or other delicate anatomical structures at step 620. Prior to starting the surgical procedure, a camera 150 is inserted within the patient. During the surgical procedure, a real time video signal is received by the AR controller 200 via video processor at step 625. The AR controller 200 augments the safety zone onto the video signal at step 630. The safety zone is then displayed with the video signal at step 635. For example, the safety zone may be shown as a yellow area around an organ. The location of the surgical tool 10 within the patient is measured at step 640 using the position calculator 310, speed calculator 360, and other sensors 315. The AR controller determines if the surgical tool 10 is within the safety zone at step 645. If the surgical tool 10 is not within the safety zone, then the system measures the new location of the surgical tool 10. If the surgical tool is within the safety zone, then the AR controller notifies the surgeon at step 650. This notification may be haptic feedback. The haptic mechanism may be an asynchronous motor that vibrates in a pulsating manner. In one embodiment, the vibrations are at a frequency of about 30 Hz or above, providing a displacement having an amplitude of 1.5 mm or lower to limit the vibratory effects from reaching the end effector assembly 100. The haptic feedback can be increased or decreased in intensity. For example, the intensity of the feedback may be used to indicate that the forces on the instrument are becoming excessive. In alternative embodiments, the user feedback may be visual and/or audible feedback. The process 600 then keeps measuring the location of the surgical tool 10 until the surgical procedure is turned off.

Figure 7A:
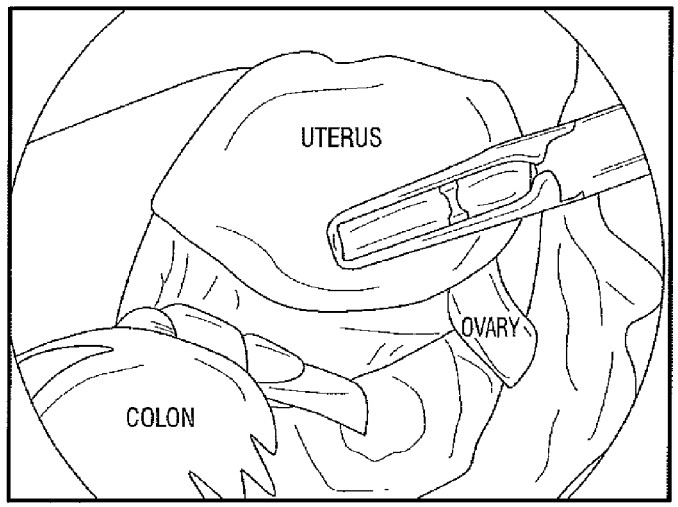
FIG. 7A-C illustrate examples of augmented video displays according to an embodiment of the present disclosure.
Figure 7B:
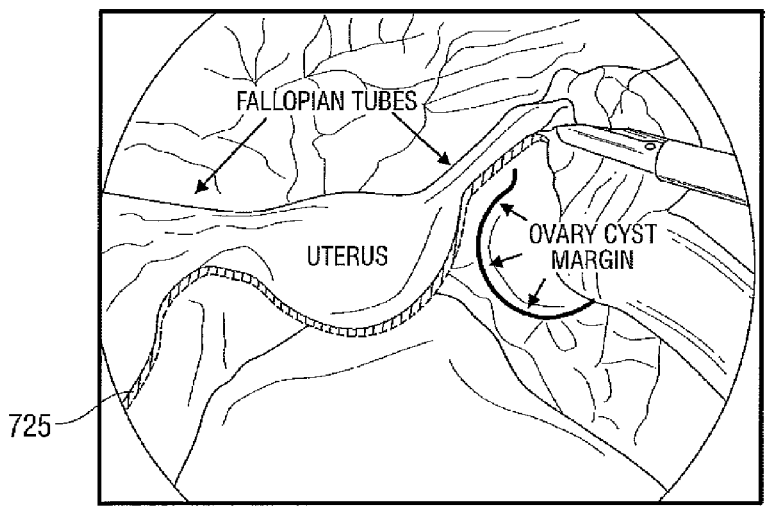
Figure 7C:
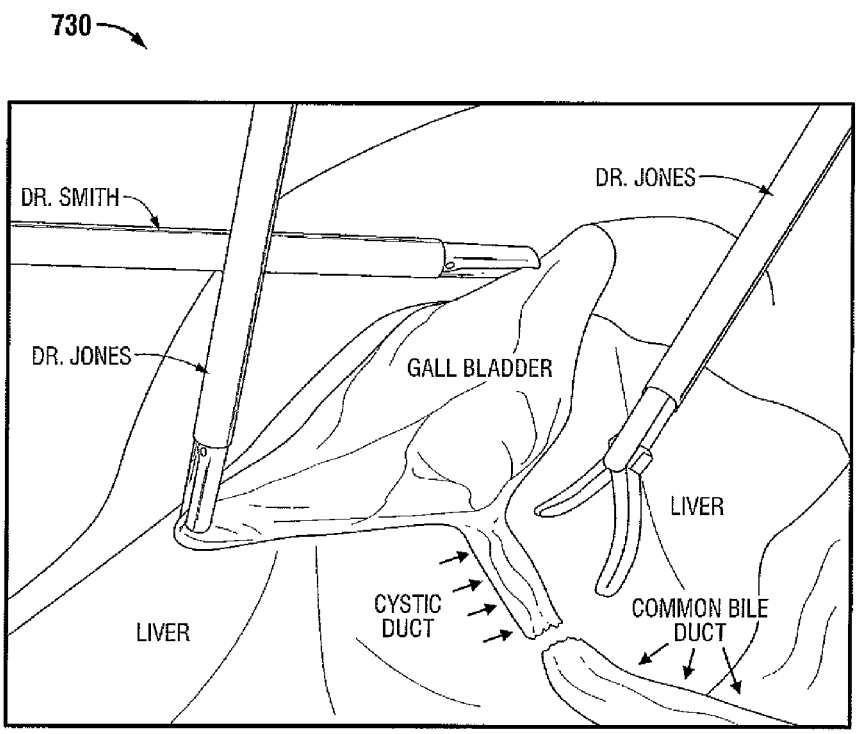

FIG. 7(A)-(C) illustrate examples of an augmented video display according to another embodiment of the present disclosure. FIG. 7A shows an example of an augmented video display 710 where the appropriate labels for organs and tissue are overlaid onto a real time video image. In this example, the uterus, colon, bowel, ovary, and fallopian tubes are labeled on the display screen 710. A second example, FIG. 7B, shows an augmented video display 720 with the margins for an ovary cyst overlaid on the real time video signal. Additionally, the augmented video display 720 displays the appropriate labels for organs and tissue. For example, the ovary cyst margin may guide a surgeon to where to cut. Further, the display 720 may include a safety boundary 725 around delicate tissue or organs. For example, a cross hatched area may be displayed around the fallopian tubes. FIG. 7C shows an augmented video display 730 with labels for each surgeon using a corresponding instrument overlaid onto the real time video image. The labels on the tools can be entered by a user or the instrument 10 may include a radio frequency identity (RFID) chip that communicates with RFID chip on the surgeon to allow automatic marking of tools. Additionally, FIG. 7C shows labels of tissue and organs by labeling the gall bladder, liver, cystic duct, and common bile duct. Further, as the video image changes, the location of the augmented reality information moves to the appropriate location as the computer 180 or microcontroller 250 are constantly or periodically analyzing the video image to update the location of augmented reality information. The video image may be analyzed about every 0.1 ms or other suitable increment necessary to provide proper information to the surgeon.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for augmenting data onto a video image, the method comprising:
   generating a pre-operative image of an anatomical section of a patient;
   generating a video image of a surgical site within the patient, wherein the video image includes an image of at least a portion of a surgical tool operated by a user;
   processing the pre-operative image to generate data about the anatomical section of the patient, the data including a label for the anatomical section and a peripheral margin of at least a portion of the anatomical section, the peripheral margin configured to guide a surgeon to a cutting location relative to the anatomical section;
   embedding the data and an identity of the user within the video image to supply an augmented reality display to the user about the anatomical section of the patient;
   sensing a loading condition on the surgical tool;
   generating a feedback signal based on the sensed loading condition; and
   updating, in real time, the data and a location of the identity of the user operating the surgical tool embedded within the video image in response to a change in a location of the surgical tool within the video image.

2. The method according to claim 1, wherein the pre-operative image is generated from at least one of a magnetic resonance image (MRI), tomography, x-ray, ultrasound, thermography, single photon emission computed tomography (SPECT), photoacoustic imaging, myocardial perfusion imaging (MPI), gamma camera, or fluoroscopy.

3. The method according to claim 1, wherein the anatomical section is at least one of an organ, bone, tumor, vessel, tissue, muscle, or artery.

4. The method according to claim 1, wherein processing the pre-operative image includes computing a safety zone around at least a portion of the anatomical section.

5. The method according to claim 4, further comprising:
   determining if the surgical tool is within the safety zone and generating a notification to the user if the surgical tool is within the safety zone.

6. The method according to claim 5, wherein the notification includes haptic feedback, the intensity of the haptic feedback directly correlating to a proximity of the surgical tool within the safety zone.

7. The method of claim 1, wherein generating the feedback signal includes generating haptic feedback.

8. The method of claim 1, further comprising:
   changing an intensity of the feedback signal based on the sensed loading condition.

9. The method of claim 1, wherein sensing the loading condition on the surgical tool includes sensing a force applied to tissue by the surgical tool.

10. The method of claim 1, wherein sensing the loading condition on the surgical tool includes sensing impedance.

11. The method of claim 1, further compromising:
    determining a change in the anatomical section engaged by the surgical tool based on the sensed loading condition on the surgical tool.

12. The method of claim 1, further comprising:
    detecting an abnormal loading condition on the surgical tool based on the sensed loading condition on the surgical tool.

13. A method for generating a safety zone onto a video signal, the method comprising:
    storing a pre-operative image of an anatomical section of a patient;
    analyzing the pre-operative image to determine a safety zone around an anatomical body within the patient and generate data about the anatomical body of the patient, the data including a label for the anatomical body and a peripheral margin of at least a portion of the anatomical body, the peripheral margin configured to guide a user to a cutting location relative to the anatomical body, wherein the anatomical body is located within the anatomical section;
    receiving the video signal from a camera located within the patient during a surgical procedure, wherein the video signal includes a signal associated with an image of at least a portion of a surgical tool operated by the user;
    augmenting the safety zone, the data, and an identity of the user operating the surgical tool onto the video signal;
    displaying the video signal with the safety zone and the identity of the user operating the surgical tool;
    determining a location of the surgical tool within the displayed video signal;
    generating a notification to the user operating the surgical tool based on the location of the surgical tool relative to the safety zone;
    sensing a loading condition on the surgical tool;
    generating a feedback signal based on the sensed loading condition; and
    updating, in real time, the data and a location of the augmented identity of the user operating the surgical tool on the displayed video signal in response to a change in the location of the surgical tool within the displayed video signal.

14. The method according to claim 13, wherein the notification is at least one of an audible notification, a visual notification, or haptic feedback.

15. The method according to claim 13, wherein the pre-operative image is generated from an image diagnosing system and the image diagnosing system includes at least one of a magnetic resonance image (MRI), tomography, x-ray, ultrasound, thermography, single photon emission computed tomography (SPECT), photoacoustic imaging, myocardial perfusion imaging (MPI), gamma camera, or fluoroscopy.

16. The method according to claim 13, wherein the anatomical body is at least one of an organ, a bone, a tumor, vessel, tissue, muscle, or artery.

17. A system for augmenting data onto a real time video signal, comprising:
    a pre-operative image generated of an anatomical section of a patient;
    a camera configured to send the real time video signal from the patient to the controller, wherein the camera is placed within the patient prior to starting surgery and the real time video signal includes an image of at least a portion of a first surgical tool operated by a first user;
    a sensor disposed on the first surgical tool and configured to sense a loading condition on the first surgical tool and to generate a feedback signal based on the sensed loading condition;
    the controller configured to analyze the pre-operative image and the feedback signal from the sensor to gather data about the anatomical section, and to augment an identity of the first user and the data about the anatomical section onto the real time video signal, the data including a label for the anatomical section and a peripheral margin of at least a portion of the anatomical section, the peripheral margin configured to guide the first user to a cutting location relative to the anatomical section; and
    a user interface configured to display the real time video signal and the augmented data, wherein the controller is further configured to identify the first surgical tool as under control of the first user on the user interface, and to update, in real time, the data and a location of the identity of the first user on the user interface in response to a change in a location of the first surgical tool within the video signal.

18. The system according to claim 17, wherein the controller is further configured to compute a location of the anatomical section.

19. The system according to claim 17, wherein the pre-operative image is generated from image diagnosing system that includes at least one of a magnetic resonance image (MRI), tomography, x-ray, ultrasound, thermography, single photon emission computed tomography (SPECT), photoacoustic imaging, myocardial perfusion imaging (MPI), gamma camera, or fluoroscopy.

20. The system according to claim 17, wherein the anatomical section is at least one of an organ, a bone, a tumor, vessel, tissue, muscle, or artery.

21. The system according to claim 17, wherein the controller is further configured to compute a safety zone around at least a portion of the anatomical section to determine if the first surgical tool is within the safety zone, and to generate a notification if the first surgical tool is within the safety zone.

22. The system according to claim 21, further comprising:
    a haptic mechanism configured to send haptic feedback to the first user, the intensity of the haptic feedback directly correlating to the proximity of the first surgical tool within the safety zone.

23. The system according to claim 17, wherein the real time video signal includes an image of at least a portion of a second surgical tool operated by a second user, and the controller is further configured to identify the second surgical tool as under control of the second user on the user interface.

24. The system according to claim 23, wherein a label for at least one of the first surgical tool or the second surgical tool is automatically generated or inputted through the user interface and augmented onto the real time video.

25. A method for augmenting a video image of a patient, comprising:
    processing a pre-operative image of an anatomical section of a patient to generate data about the anatomical section of the patient, the data including a label for the anatomical section and a peripheral margin of at least a portion of the anatomical section, the peripheral margin configured to guide a user to a cutting location relative to the anatomical section;
    identifying at least one anatomical object in the processed pre-operative image;
    identifying at least one of the at least one anatomical objects in the processed pre-operative image as a delicate;
    receiving a video image from a camera disposed within the patient;
    displaying in the video image at least a portion of a surgical tool operated by the user;
    augmenting onto the video image a safety boundary around the at least one anatomical object identified as delicate to prevent the user from treating the at least one anatomical object identified as delicate with the surgical tool;
    embedding the data and an identity of the user within the video image to supply an augmented reality display to the user about the anatomical section of the patient;
    determining a location of the surgical tool relative to the safety boundary;
    generating a notification to the user based on the determined location of the surgical tool;
    sensing a loading condition on the surgical tool;
    generating a feedback signal based on the sensed loading condition; and
    updating, in real time, the data and a location of the identity of the user operating the surgical tool embedded within the video image in response to a change in a location of the surgical tool within the video image.

26. The method according to claim 25, further comprising:
    determining a location and a margin of the at least one anatomical object identified in the processed pre-operative image.

27. The method according to claim 26, further comprising:
    displaying in the video image the determined margin.

28. The method according to claim 26, further comprising:
    treating the at least one anatomical object identified in the processed pre-operative image with the surgical tool based on the determined location and margin.

29. The method according to claim 25, further comprising:
    generating a label for at least one of the at least one anatomical objects identified in the processed pre-operative image.

30. The method according to claim 25, further comprising:
    displaying in the video image a label identifying the user operating the surgical tool.

31. The method according to claim 25, further comprising:
    displaying in the video image at least a portion of the determined safety boundary as a cross-hatched area.

32. A method for augmenting a video image of a patient, the method comprising:
    processing a pre-operative image of an anatomical section of a patient;
    identifying at least one anatomical object in the processed pre-operative image;
    generating a label for at least one of the at least one anatomical objects identified in the processed pre-operative image;

determining a location and a margin of the at least one anatomical object identified in the processed pre-operative image, the margin configured to guide a user to a cutting location relative to the at least one anatomical object;
identifying at least one of the at least one anatomical objects in the processed pre-operative image as delicate;
determining a safety boundary around the at least one anatomical object identified as delicate;
sensing a loading condition on the surgical tool;
generating a feedback signal based on the sensed loading condition;
receiving a video image from a camera disposed within the patient;
embedding the label, the margin, and an identity of the user within the video image to supply an augmented reality display to the user about the anatomical section of the patient;
overlaying the generated label and the determined margin on the video image;
overlaying at least a portion of the determined safety boundary on the video image to prevent the user from treating the at least one anatomical object identified as delicate with the surgical tool; and
updating, in real time, the label, the margin, the identity of the user and a location of the identity of the user operating the surgical tool embedded within the video image in response to a change in a location of the surgical tool within the video image.

* * * * *